United States Patent
Kerc et al.

(10) Patent No.: US 9,089,486 B2
(45) Date of Patent: Jul. 28, 2015

(54) PROCESS FOR THE PREPARATION OF A PHARMACEUTICAL COMPOSITION COMPRISING EZETIMIBE

(75) Inventors: Janez Kerc, Ljubljana (SI); Miha Homar, Ljubljana (SI); Polona Jurkovic, Ljubljana (SI)

(73) Assignee: LEK PHARMACEUTICALS D.D., Ljubljana (SI)

( * ) Notice: Subject to any disclaimer, the term of this patent is extended or adjusted under 35 U.S.C. 154(b) by 116 days.

(21) Appl. No.: 13/147,956

(22) PCT Filed: Feb. 5, 2010

(86) PCT No.: PCT/EP2010/051401
§ 371 (c)(1),
(2), (4) Date: Dec. 27, 2011

(87) PCT Pub. No.: WO2010/089361
PCT Pub. Date: Aug. 12, 2010

(65) Prior Publication Data
US 2012/0135976 A1    May 31, 2012

(30) Foreign Application Priority Data
Feb. 6, 2009   (EP) .................................... 09152272

(51) Int. Cl.
*A61K 9/14* (2006.01)
*A61K 9/20* (2006.01)
*A61K 31/366* (2006.01)
*A61K 31/397* (2006.01)
*A61P 3/06* (2006.01)

(52) U.S. Cl.
CPC ............... *A61K 9/145* (2013.01); *A61K 9/2018* (2013.01); *A61K 9/2095* (2013.01)

(58) Field of Classification Search
CPC .... A61K 9/145; A61K 9/2018; A61K 9/2095
USPC ...................... 424/464, 489; 514/210.02, 460
See application file for complete search history.

(56) References Cited

U.S. PATENT DOCUMENTS

| 2007/0275052 | A1  | 11/2007 | Mahajan et al. |         |
|--------------|-----|---------|----------------|---------|
| 2010/0291207 | A1* | 11/2010 | Gat et al.     | 424/465 |
| 2011/0262497 | A1* | 10/2011 | Injac et al.   | 424/400 |

FOREIGN PATENT DOCUMENTS

| EP | 1 741 427 A      | 1/2007 |
| WO | WO 2005/067903 A | 7/2005 |
| WO | WO 2007/054975 A | 5/2007 |
| WO | WO 2007/103453 A | 9/2007 |
| WO | WO 2009/016358 A | 2/2009 |

OTHER PUBLICATIONS

Lacey J. Appl. Chem. 1954, 4, 257-268.*
Ameye et al. European J. Pharm. Sci. 2002, 17, 247-251.*
Ghorab et al. AAPS PharmSciTech 2007, 8 (4), article 84, E1-E9.*

* cited by examiner

*Primary Examiner* — Sreeni Padmanabhan
*Assistant Examiner* — Irina Neagu
(74) *Attorney, Agent, or Firm* — Arent Fox LLP (57) ABSTRACT

The present invention belongs to the field of pharmaceutical industry and relates to a process for preparing dosage forms containing ezetimibe, comprising the steps of:
a) providing a composition comprising ezetimibe,
b) sieving a composition comprising a composition of step (a),
c) shear mixing of the composition after step (b), preferably the mixing of the composition is carried out by high shear mixing,
d) formulation into a dosage form.

The present invention also relates to dosage forms containing ezetimibe and ezetimibe and simvastatin, which have been prepared according to the process according to the invention.

9 Claims, 2 Drawing Sheets

PROCESS FOR THE PREPARATION OF A PHARMACEUTICAL COMPOSITION COMPRISING EZETIMIBE

CROSS-REFERENCE TO RELATED APPLICATION

This application is a National Stage entry of International Application No. PCT/EP2010/051401, filed Feb. 5, 2010, which claims priority to European Application No. 09152272.2, filed Feb. 6, 2009, the entire specifications, claims and drawings of which are incorporated herewith by reference.

FIELD OF THE INVENTION

The present invention belongs to the field of pharmaceutical industry and relates to a process for preparing dosage forms comprising ezetimibe. The present invention furthermore relates to dosage forms prepared according to the process of the invention, as well as to the use of the dosage forms for the treatment of hypercholesterolemia.

DESCRIPTION OF THE BACKGROUND ART

High blood or plasma cholesterol levels or hypercholesterolemia represent a common disease pattern preliminary in the well situated countries of the western hemisphere. Cholesterol may cause a "hardening of the arteries" so that arteries become narrowed and blood flow to the heart is slowed down or even blocked with the consequence that provision of oxygen to the organs is constrained. Hypercholesterolemia has been implicated in atherosclerosis, heart attack, and stroke and is one of several conditions that may lead to coronary artery disease, which is the leading cause of death in the United States, accounting for approximately 600,000 deaths per year. The risk group includes the overweight, smokers, those with a poor diet (e.g. one rich in saturated fats), those who take inadequate exercise and suffering from stress. For such risk individuals, as well as those tested and found to have unduly high plasma cholesterol levels, a variety of treatments have been proposed, e.g. changes in diet and habits, increased exercise, etc. However, such treatments are not always easy to enforce and there exist a need for improved medicinal treatments which are effective at reducing plasma cholesterol levels.

In above mentioned cases, ezetimibe can be prescribed, since it is indicated mainly for primary hypercholesterolemia (administered alone or in combination with an HMG-CoA reductase inhibitor), homozygous familial hypercholesterolemia (administered with atorvastatin or simvastatin) and homozygous sitosterolemia [PDR prescribing information for Zetia®]. Ezetimibe is sold under the brand name Zetia®, which is marketed by Merck/Schering-Plough Pharmaceuticals. Zetia® is available as a tablet for oral administration containing 10 mg of ezetimibe. The inactive ingredients of Zetia® are reported to be croscarmellose sodium, lactose monohydrate, magnesium stearate, microcrystalline cellulose, povidone, and sodium lauryl sulfate. The recommended dose is 10 mg once daily, administered with or without food according to the Zetia® label.

Ezetimibe, a white crystalline powder disclosed in EP 0 720 599, is reported to be freely to very soluble in ethanol, methanol, and acetone, and practically insoluble in water. Further it is reported to have a melting point of about 163° C. and to be stable at ambient temperature. The mechanism of action of ezetimibe on absorption and resorption inhibition of cholesterol involves increased excretions of cholesterol and its intestinally generated metabolites with the faeces. This effect results in lowered body cholesterol levels, increased cholesterol synthesis, and decreased triglyceride synthesis. The increased cholesterol synthesis initially provides for the maintenance of cholesterol levels in the circulation, levels that eventually decline as the inhibition of cholesterol absorption and resorption continues. The overall effect of drug action is the lowering of cholesterol levels in the circulation and tissues of the body.

Other commonly used compounds for the treatment or prevention of high cholesterol levels in individuals are the statins, such as fluvastatin, simvastatin, and lovastatin. Among the group of statins, particularly simvastatin exhibited good results in the treatment of conditions characterized by high cholesterol levels. Methods for its preparation are disclosed in e.g. in EP 0 033 538, EP 0 351 918, and EP 0 299 656. Simvastatin exerts a cholesterol reducing effect by inhibiting the conversion of 3-hydroxy-3-methylglutarylcoenzyme A (HMG-CoA) to mevalonate, an early step in the biosynthetic pathway of cholesterol. Additionally, simvastatin reduces the amount of very-low density lipoproteins (VLDL) and triglycerides (TG) and increases high-density lipoprotein cholesterol (HDL-C) and is thus capable to counteract diseases like atherosclerosis. Simvastatin is marketed worldwide and sold under the trade name ZOCOR®. ZOCOR® tablets contain simvastatin, anhydrous lactose, microcrystalline cellulose (fillers), pregelatinized maize starch (disintegrant), magnesium stearate (lubricant), butylated hydroxyanisol (BHA), citric acid monohydrate and ascorbic acid (antioxidants).

In order to provide improved medication combination products, such as a combination of ezetimibe and simvastatin, were considered. Such a combination is marketed, for example, in the USA under the trade name VYTORIN®. The commercially available VYTORIN® tablets contain ezetimibe, simvastatin, lactose monohydrate, microcrystalline cellulose (fillers), hydroxylpropyl methylcellulose (binder), croscarmellose sodium (disintegrant), magnesium stearate (lubricant), butylated hydroxyanisol (BHA), citric acid monohydrate and propyl gallate (antioxidants). For the time being, combinations comprising 10 mg of ezetimibe each and 10, 20, 40 and 80 mg simvastatin, respectively, are commercially available. Such a combination medicament has been proven to be effective in the treatment and/or prevention of atherosclerosis and related conditions.

When a solid dosage form with a poorly soluble drug (e.g. ezetimibe) is taken orally, the drug must dissolve in aqueous gastrointestinal fluids in, e.g., patient's stomach, before it can exert a therapeutic effect. A recurring problem with solid oral dosage forms comprising poorly water soluble drugs (e.g. ezetimibe) is that the rate of dissolution of the drug limits its biological availability.

Known methods for preparing formulations containing ezetimibe mostly use wet granulation, which is the method of choice for the preparation of ezetimibe/simvastatin combinations.

EP 1 849 459 discloses compositions containing ezetimibe with improved solubility of ezetimibe and increased bioavailability, methods of their preparation, and method of treatment using the same. An ezetimibe composition according to this document may be prepared, for example, by co-milling ezetimibe with at least one hydrophilic excipient.

WO 2008/101723 discloses a pharmaceutical composition comprising at least one cholesterol absorption inhibitor such as ezetimibe with improved dissolution rate and exhibiting a high bioavailability in amorphous form and at least one hydrophilic polymer. In one embodiment, the amorphous cholesterol absorption inhibitor is finely dispersed in the hydrophilic polymer by means of spray-drying.

WO 2006/134604 describes stable antihyperlipoproteinemic combinations of solid oral pharmaceutical formulations containing ezetimibe, HMG-CoA reductase inhibitor, disintegrants and glidants. During manufacture, a milling step in order to achieve the desired particle size distribution is carried out. However, in such milling steps often agglomerates of the particles are formed. This can negatively influence the properties of the formulations.

WO 2007/003365 describes stable pharmaceutical compositions containing simvastatin and/or ezetimibe and their preparation. Some embodiments disclose the mixing of a part of the ingredients in a high shear mixer and granulation, followed by a drying- and sieving-step of the obtained granules.

U.S. Pat. No. 7,229,982 B2 discloses a pharmaceutical composition comprised of a cholesterol absorption inhibitor and an HMG-CoA reductase inhibitor, one or more antioxidants, microcrystalline cellulose, hydroxypropyl methylcellulose, magnesium stearate and lactose.

However, despite the above described methods and preparations of formulations containing ezetimibe, there is a need for an improved process for the preparation of a dosage form containing ezetimibe, in particular with regard to a dissolution profile that allows for a good effectivity and with regard to an improved processability.

SUMMARY OF THE INVENTION

The present invention provides the following aspects, subject-matters and preferred embodiments, which respectively taken alone or in combination, further contribute to solving the object of the present invention:

(1) A process for preparing a dosage form comprising ezetimibe, the process comprising the steps of:
 a) providing a composition comprising ezetimibe, optionally blended with excipients, preferably with hydrophilic excipients,
 b) sieving a composition comprising a composition provided by step (a),
 c) shear mixing of the composition after step (b) to obtain a more homogenous distribution of the components of the composition,
 d) formulation into a dosage form.

(2) The process according to item 2, wherein the composition provided by sieving in step b) is directly used in step c).

This means that no further compounds are added to the composition after sieving and prior to the shear mixing. In other terms, step c) directly succeeds step b) without carrying out further steps like the addition of compounds, heating the composition, dissolving the composition or the compounds and the like.

(3) The process according to item 1 or 2, wherein step (c) is preferably carried out by high shear mixing.

Preferably, the shear mixing, preferably the high shear mixing, of the particles comprising ezetimibe obtained after the sieving step does not result in a reduction of the d(0.9) particle size of said particles subjected to shear mixing of more than 20%, further preferred of more than 10%, even further preferred of more than 5%.

(4) The process according to any of items 1 to 3, wherein process step (d) comprises direct compression.

(5) A process for preparing a dosage form comprising ezetimibe, the process comprising the steps of:
 a) providing a composition comprising ezetimibe,
 b) sieving a composition comprising a composition provided by step (a),
 c) direct compression of the composition after step (b).

(6) The process according to any of items 1 to 5 wherein essentially changing the particle size of ezetimibe is avoided, preferably a reduction of the particle size is avoided.

(7) The process according to any of items 1 to 6 wherein the conduction of a milling step is omitted.

(8) The process according to any of items 1 to 7 wherein the ezetimibe in step (a) and in the dosage form is in a crystalline form.

(9) The process according to any of the previous items wherein the composition of step (a) additionally comprises at least one hydrophilic excipient.

(10) The process according to item 9 wherein the ezetimibe:hydrophilic excipient weight ratio is in a range of from about 1:1 to about 1:100, preferably in a range of from about 1:5 to about 1:80, most preferably in a range of from about 1:10 to about 1:60.

(11) The process according to item 9 or 10 wherein the at least one hydrophilic excipient is selected from the group consisting of polyethylene glycols, poloxamers, polysaccharides, saccharides or mixtures thereof (e.g. StarLac® or IsoMalt®), preferably the hydrophilic excipient is selected from the group consisting of lactose, spray dried lactose and starch, particularly the hydrophilic excipient is spray dried lactose.

(12) The process according to any of the previous items wherein simvastatin is used in the process of preparing the dosage form.

(13) The process according to any one of the previous items wherein at least one further excipient is used in the process of preparing the dosage form.

(14) The process according to item 13 wherein the at least one further excipient is selected from the group consisting of diluents, binding agents, fillers, disintegrants, lubricants, sweeteners, glidants, flavourings and colouring agents.

(15) The process according to item 14 wherein
 the fillers are selected from the group consisting of different grades of starches, such as maize starch, potato starch, rice starch, wheat starch, pregelatinized starch, fully pregelatinized starch, cellulose, such as microcrystalline cellulose or silicified microcrystalline cellulose, mannitol, erythritol, lactose, such as lactose monohydrate and lactose anhydrous or spray dried lactose, calcium, such as calcium hydrogenphosphate, sorbitol, and xylitol, particularly preferred, the fillers are selected from the group consisting of pregelatinized starch, microcrystalline cellulose, silicified microcrystalline cellulose, lactose monohydrate, and spray dried lactose;
 the disintegrants are selected from the group consisting of carmellose calcium, carboxymethylstarch sodium, croscarmellose sodium, croscarmellose sodium salt (cellulose carboxymethylether sodium salt, crosslinked), starch, such as sodium starch glycolate or corn starch, crosslinked polyvinylpyrrolidone (crospovidone), and low-substituted hydroxypropylcellulose, particularly preferred, the disintegrants are selected from the group consisting of sodium starch glycolate, croscarmellose sodium salt, and croscarmellose sodium;
 the lubricants are selected from the group consisting of stearic acid, talc, sodium stearyl fumarate and magnesium stearate, particularly preferred, the lubricant is magnesium stearate;
 the binding agents are selected from the group consisting of polyvinyl pyrrolidone (Povidone), copolymers of vinylpyrrolidone with other vinyl derivatives (Copovidone), hydroxypropyl methylcellulose, methylcellulose, hydroxypropylcellulose, powdered acacia, gelatin, guar gum, carbomer such as carbopol, polymethacrylates and starch, particularly preferred, the binding agents are selected from the group consisting of hydroxypropyl methylcellulose, hydroxypropylcellulose and copovidone;

the diluents are selected from carbohydrates such as monosaccharides like glucose, oligosaccharides like sucrose, anhydrous lactose and lactose monohydrate, and sugar alcohols like sorbitol, mannitol, erythrol, and xylitol, particularly preferred the diluent is sorbitol;

the glidants are selected from the group consisting of colloidal silica, hydrophobic colloidal silica and magnesium trisilicat, such as talcum, particularly preferred the glidants are selected from the group consisting of colloidal silica and hydrophobic colloidal silica; and/or the sweeteners are selected from the group consisting of aspartame, saccharin sodium, dipotassium glycyrrhizinate, aspartame, stevia, thaumatin, and the like.

(16) The process according to any of items 13 to 15 wherein the further excipients microcrystalline cellulose, croscarmellose sodium, hydroxypropylcellulose and colloidal silica are added.

(17) The process according to any of items 13 to 16 wherein the simvastatin and/or the at least one further excipient is added to the composition in step (c) and then, optionally a further step of, shear mixing, preferably high shear mixing, is carried out.

(18) The process according to any of the previous items wherein step (c) directly succeeds step (b).

(19) The process according to any of the previous items wherein the size of the sieve in the sieving step is between 125 mesh and 4 mesh.

(20) The process according to any of the previous items wherein the shear mixing is carried out at a paddle speed of at least 100, for example at a paddle speed of 100 to 1500, preferably of 300 to 1200 RPM, and more preferably of 500 to 1000 RPM.

(21) The process according to any of the previous items wherein the addition of water or alcohol is avoided, and optionally the addition of any liquid substance is avoided.

(22) A dosage form, obtained according to a process according to any of items 1 to 21.

(23) The dosage form according to item 22, for use in the prophylaxis or treatment of hypercholesterolemia.

(24) A composition comprising ezetimibe, obtained according to a process comprising the steps of:

a) sieving a composition comprising ezetimibe, optionally blended with hydrophilic excipients, b) shear mixing of the composition after step (a) to provide a fine particle distribution, preferably the shear mixing of the composition is carried out by high shear mixing.

(25) The composition according to item 24 wherein the composition is obtained under dry conditions, preferably the process does not comprise the addition of water or alcohol, preferably no solvent is added, and optionally no liquid substance is added.

(26) The composition according to item 24 or 25, for use in the prophylaxis or treatment of hypercholesterolemia.

(27) A composition comprising ezetimibe and simvastatin, obtained according to a process comprising the steps of:

a) sieving a composition comprising ezetimibe, optionally blended with hydrophilic excipients b) mixing of the composition after step (a) to provide a fine particle distribution, preferably the mixing of the composition is carried out by shear mixing, wherein simvastatin is added prior or after step a), preferably during the mixing process in step b).

(28) The composition according to item 27, wherein the composition is obtained under dry conditions, preferably the process does not comprise the addition of water or alcohol, preferably no solvent is added, and optionally no liquid substance is added.

(29) The composition according to item 27 or 28, wherein in a further process step c) the composition resulting from process step b) is formulated into a dosage form, preferably the further process step c) comprises direct compression.

DETAILED DESCRIPTION OF THE INVENTION

The present invention is now described in more detail by preferred embodiments and examples, which are however presented for illustrative purpose only and shall not be understood as limiting the scope of the present invention in any way.

It was surprisingly found that the inventive process using a sieving step followed by a shear mixing step, can provide pharmaceutical formulations having an improved dissolution profile compared to formulations prepared by using a mixing step or a sieving step respectively alone or a mixing step followed by a sieving step. Even more surprisingly, if the order of the technological steps is reversed, i.e. if the shear mixing step was followed by sieving, the dissolution profiles of ezetimibe are lower compared to the dissolution profiles of formulations prepared by using a sieving step followed by a shear mixing step. According to the present invention, the term "shear mixing" denotes the process of mixing a composition to obtain a more homogenous distribution of the components of the composition, preferably the term "shear mixing" denotes the process of shear mixing a composition comprising two or more components to the effect that a relatively finer and more homogenous distribution of components in the composition, e.g. a finer particle distribution, is reached compared to the situation prior to shear mixing. In particular, it is avoided that some portions of the composition contain excessive amounts of some or all of the components being present in the composition. Preferably the shear mixing is carried out by a high shear mixing.

The shear mixing within the meaning of the present invention is distinct from a less intense "blending" as carried out in known processes. Different equipment is used for a blending process and for a shear mixing process, respectively. Significantly, such different equipment is associated with different magnitudes of rotation (RPM, rotations per minute) of a mixing means. For instance, for blending a blender such as V-blender is used which is typically operated at a rotation speed of about 30 RPM. Contrary thereto, the shear mixing process applied according to the present invention is performed at a significantly higher rotation speed of about 100 RPM or more. Rotation is preferably accomplished by a rotating element in the equipment, typically one or more paddle or similar means. For the shear mixing step used in the present invention, a high shear mixer is preferred. It has been found that, when combined with the other process steps as disclosed herein, a more intense mixing using a higher paddle speed positively influences the dissolution properties of the resulting formulations compared to formulations prepared by only blending or gentle mixing processes.

It has been found that the removal of either step (i.e sieving or thorough mixing) results in tablets with poorer dissolution profiles. Both steps, performed in the correct order, therefore significantly contribute to achieve desired dissolution profiles. Without wishing to be bound by any theory, it is presently assumed that the desired increase in the dissolution rate is due to reduction of the agglomerates of ezetimibe and closer association of ezetimibe with appropriated blended excipients, notably with hydrophilic excipients, which increases the specific surface of the active drug substance available for the dissolution. Further surprisingly, the above mentioned process can be carried out without further or additional reduction of the particle size of ezetimibe such as intensive milling procedures to further increase the surface area of the particles, which theoretically might also contribute to the increase in the dissolution rate. However extremely micronized drug powders are very cohesive due to high energy milling processes causing significant dislocation of crystal structure on the particle surface. Such particles tend to agglomerate during the solid state processing, leading to poorer dissolution performance. Hence, the process according to the present invention allows to obtain excellent ezetimibe dissolution performance while starting the process with appropriate particle sizes thereof, i.e. without the need to perform extra or excessive milling which might otherwise increase the tendency to agglomerization of ezetimibe particles.

Unexpectedly the sieving and shear mixing and especially high shear mixing, of a composition comprising ezetimibe and preferably a hydrophilic excipient, like lactose, is suitable to provide formulations having even further improved properties.

It has also been found that pharmaceutical dosage forms containing ezetimibe can advantageously be prepared by carrying out a sieving step of the ezetimibe composition followed by a direct compression step. This surprisingly results in tablets with an improved dissolution profile of ezetimibe. Since the dissolution of ezetimibe is a critical step with respect to the therapeutic effect, these tablets are considered to have a good therapeutic effect. Moreover, applying a direct compression step allows avoiding the use of water and organic solvents such as alcohol or aqueous solvent mixtures, which is beneficial when using solvent sensitive active compounds like ezetimibe and/or simvastatin. Moreover, time consuming and economically demanding drying steps in the preparation of solid dosage forms are no longer necessary. Although direct compression is a challenging technology and therefore normally not the method of choice, it advantageously is the fastest and most cost effective way of tablet preparation and if performed after sieving (and in a preferred embodiment after a subsequent shear mixing) yet provides good dissolution profiles of ezetimibe. It has also been found that carrying out a process according to the invention for preparing a dosage form comprising ezetimibe and simvastatin provides an improved stability, especially of simvastatin in the dosage form. Moreover any solvent, such as water and/or alcohol or other solvents, optionally even any liquid, as a potential source of impurities or as potential factor affecting stability of either ezetimibe or simvastatin, or both, can be excluded.

The present invention relates to a process for preparing a dosage form comprising the step of providing a composition containing ezetimibe (step (a) of the process). The composition can be prepared according to known methods by blending the ingredients of the composition.

According to the invention, the ezetimibe in step (a) and in the dosage form can be in amorphous or crystalline modification. However, it is preferred to use ezetimibe in a crystalline form in step (a). In one embodiment of the invention, the process does not comprise the use of any water or alcohol, optionally obviates the use of any solvent and furthermore of any liquid substance and, therefore, the modification of the crystalline ezetimibe used is not altered in the process. Therefore it is possible to start from crystalline ezetimibe, which will then also be present in the final dosage form.

It is additionally preferred that the composition comprising ezetimibe from step (a) is blended with excipients, preferably at least one hydrophilic excipient. Preferably said hydrophilic excipient is selected from the group consisting of polyethylene glycols, poloxamers, polysaccharides, saccharides or mixtures thereof (e.g. StarLac® or IsoMalt®), more preferably the hydrophilic excipient is selected from the group consisting of lactose, spray dried lactose and starch, particularly the hydrophilic excipient is spray dried lactose. In a preferred embodiment of the invention, the composition in step (a) consists of ezetimibe and at least one hydrophilic excipient, further preferred the composition consists of ezetimibe and one hydrophilic excipient, preferably lactose. The use of spray dried lactose is especially preferred. Particularly preferred, the composition comprising, or consisting of, ezetimibe and the at least one hydrophilic excipient is prepared by combining ezetimibe and the at least one hydrophilic excipient in a dry state followed by sieving and shear mixing, preferably high shear mixing, according to the invention. Particularly preferred, the ezetimibe used in step (a) has a particle size between 1 and 30 µm, more preferably between 5 and 30 µm, even more preferably between 8 and 25 µm. Further preferred, ezetimibe and the at least one hydrophilic excipient and optional further ingredients are not compacted (which e.g. means that they are not passed through a machine like a roller compactor), milled, or dissolved in the method according to the present invention prior to the sieving and shear mixing step, preferably the high shear mixing step. Particularly preferred, the at least one hydrophilic excipients and/or further ingredients are in particulate form and do not represent liquids or viscous compounds Preferably, the shear mixing, preferably the high shear mixing, of the particles comprising ezetimibe obtained after the sieving step does not result in a reduction of the d(0.9) particle size of said particles subjected to shear mixing of more than 20%, further preferred of more than 10%, even further preferred of more than 5%.

Preferably other excipients are selected from the group consisting of diluents, binding agents, fillers, disintegrants, lubricants, sweeteners, glidants, flavourings and colouring agents. These excipients are preferably added after step (b).

According to the present invention, any fillers can be used. Preferably the fillers are selected from the group consisting of different grades of starches, such as maize starch, potato starch, rice starch, wheat starch, pregelatinized starch, fully pregelatinized starch, cellulose, such as microcrystalline cellulose or silicified microcrystalline cellulose, mannitol, erythritol, lactose, such as lactose monohydrate and lactose anhydrous or spray dried lactose, calcium, such as calcium hydrogenphosphate, sorbitol, and xylitol, particularly preferred, the fillers are selected from the group consisting of pregelatinized starch, microcrystalline cellulose, silicified microcrystalline cellulose, lactose monohydrate, and spray dried lactose.

According to the present invention, any disintegrants can be used. Preferably the disintegrants are selected from the group consisting of carmellose calcium, carboxymethylstarch sodium, croscarmellose sodium, croscarmellose sodium salt (cellulose carboxymethylether sodium salt, crosslinked), starch, such as sodium starch glycolate or corn starch, crosslinked polyvinylpyrrolidone (crospovidone), and low-substituted hydroxypropylcellulose, particularly preferred, the disintegrants are selected from the group consisting of sodium starch glycolate, croscarmellose sodium salt, and croscarmellose sodium.

According to the present invention, any lubricants can be used. Preferably the lubricants are selected from the group consisting of stearic acid, talc, sodium stearyl fumarate and magnesium stearate, particularly preferred, the lubricant is magnesium stearate.

According to the present invention, any binding agents can be used. Preferably the binding agents are selected from the group consisting of polyvinyl pyrrolidone (Povidone), copolymers of vinylpyrrolidone with other vinyl derivatives (Copovidone), hydroxypropyl methylcellulose, methylcellulose, hydroxypropylcellulose, powdered acacia, gelatin, guar gum, carbomer such as carbopol, polymethacrylates and starch, particularly preferred, the binding agents are selected from the group consisting of hydroxypropyl methylcellulose, hydroxypropylcellulose and copovidone.

According to the present invention, any diluents can be used. Preferably the diluents are selected from carbohydrates such as monosaccharides like glucose, oligosaccharides like sucrose, anhydrous lactose and lactose monohydrate, and sugar alcohols like sorbitol, mannitol, erythrol, and xylitol, particularly preferred the diluent is sorbitol.

According to the present invention, any glidants can be used. Preferably the glidants are selected from the group consisting of colloidal silica, hydrophobic colloidal silica and magnesium trisilicate, such as talcum, particularly preferred the glidants are selected from the group consisting of colloidal silica and hydrophobic colloidal silica.

According to the present invention, any sweeteners can be used. Preferably the sweeteners are selected from the group consisting of aspartame, saccharin sodium, dipotassium glycyrrhizinate, aspartame, stevia, thaumatin, and the like.

According to the present invention, any flavourings and colouring agents that are known to a person skilled in the art can be used.

Preferably the hydrophilic excipients are selected from the group consisting of polyethylene glycols, poloxamers, polysaccharides, saccharides or mixtures thereof (e.g. Star-Lac® or IsoMalt®), preferably the hydrophilic excipient is selected from the group consisting of lactose, spray dried lactose and starch, particularly the hydrophilic excipient is spray dried lactose.

It is additionally preferred that the ezetimibe:hydrophilic excipient weight ratio of the composition of step (a) is in a range of from about 1:1 to about 1:100, preferably in a range of from about 1:5 to about 1:80, most preferably in a range of from about 1:10 to about 1:60.

In a preferred embodiment of the invention, further pharmaceutically active compounds, preferably a statin and more preferably simvastatin, can be added during the process. The further pharmaceutically active compound can be suitably added to the composition of step (a), preferably it is added after step (b), and more preferably at the beginning or during step (c).

In step (b) of the process according to the invention, a composition comprising a composition of step (a) is subjected to a sieving step. While the timing of the sieving step in the whole process of the invention is significant, as such the sieving step can be carried out according to methods known to a person skilled in the art. Preferably the sieving step is carried out using a sieve with a size wherein the size of the sieve is between [125] mesh and [4] mesh, preferably between [120] mesh and [4], more preferably between [60] mesh and [10] mesh, and most preferably between [40] mesh and [16] mesh. A suitable apparatus is, for instance, Frewitt GLA-OV, Switzerland. In a preferred embodiment of the invention, the composition which is subjected to the sieving step is the composition which is directly obtained by step (a).

In step (c), the composition is subjected to a shear mixing step. With respect to the process according to the invention, step c) preferably directly succeeds step (b) without carrying out further steps like the addition of compounds, heating the composition, dissolving the composition or the compounds and the like. Preferably step (c) is carried out by high shear mixing. The shear mixing allows obtaining a more homogenous distribution of the components of the composition, especially to provide a fine particle distribution. The shear procedure can e.g. be performed for at least 2 minutes, for example 5 to 30 minutes. A suitable apparatus is, for instance, Collette Gral 25 Pro, Germany. By using an apparatus of such type or similar equipment, the paddle speed can be in the range from about 100 RPM (rotations per minute) to about 300 RPM. However, the respective appropriate paddle speed may depend on the apparatus used in order to perform the shear mixing as disclosed herein, and it is also known to a skilled person which paddle speed is suitable for which apparatus. Thus, higher rotation speeds of a mixing means are well within the ambit of the mixing step of the process of the present invention. While the timing of the mixing step in the whole process is significant and shall be observed, the mixing is thus preferably carried out at a rotation speed of a mixing element such as paddle of 100-1500 RPM, preferably of 300-1200 RPM, and more preferably of 500-1000 RPM. Furthermore, "shear" mixing may not only be achieved by a certain paddle speed, i.e. a higher paddle speed compared to the speed at which a simple blending is carried out, but that the generation of shear can also be achieved by the mechanical properties of the apparatus and/or paddle used, such as the geometry of the paddle. Upon paying attention to shear forces, a skilled person can arrange suitable apparatus means in order to obtain shear mixing independent from rotation speed, or even at paddle rotation speeds lower than indicated above, e.g below 100 RPM.

With respect to the described steps of the process according to the invention, it is possible to avoid essentially changing a given appropriate particle size of ezetimibe used as the starting substance, preferably an essential (further) reduction of the particle size can be avoided. An essential change of particle size within the meaning of the present invention denotes a change being in the range of from about 20% to about 99%, preferably of from about 30% to about 99%, more preferably of from about 40% to about 99%, and most preferably of from about 50% to about 99%. Contrary thereto, an additional milling and co-milling procedure of a given starting ezetimibe substance could lead to a significant reduction (e.g. at least further 50% reduction of the ezetimibe particle size for ezetimibe which was previously milled already) of the particle size. As described above, such a particle size reduction can affect the properties of the pharmaceutically dosage form and is, therefore, preferably avoided. While a given starting ezetimibe substance may had been milled previously to a suitable particle size, therefore, the conduction of a (further) milling step to further reduce the ezetimibe particle size is preferably omitted. By applying the teaching of the present invention, an excellent dissolution profile of ezetimibe from a final pharmaceutical composition can be achieved without the need of performing an additional milling step.

It has been unexpectedly found that the use of a sieving and a shear mixing step without essentially further reducing the particle size of ezetimibe provides dosage forms with improved properties, notably with an improved dissolution rate. Preferably a reduction of the particle size of ezetimibe of more than 20% is avoided.

Preferably, the particle size d(0.9) of ezetimibe contained in the composition obtained in step (c) is between 1 and 30 μm, more preferably between 5 and 30 μm, even more preferably between 8 and 25 μm. It is possible to abstain from further reducing the particle size of ezetimibe, which would be compromised by an increased risk of particle agglomeration and thus worsening the dissolution profile. Hence, in combination with the steps performed in the process according to the invention, the aforementioned size ranges can achieve an excellent balance between reduced tendency of agglomeration and excellent dissolution of ezetimibe in water.

In another preferred embodiment of the invention, simvastatin and/or at least one further excipient is added to the composition resulting from the mixing step (c). It is further preferred that the resulting composition is then again subjected to a further shear mixing step as described above for step (c). With this respect, the further excipients can be selected from the group of compounds as described above. Preferably the further excipients are selected from microcrystalline cellulose, croscarmellose sodium, hydroxypropylcellulose and colloidal silica. In one preferred embodiment of the invention, all of the aforementioned further excipients are used together.

According to the invention, the composition resulting from the above described process steps is formulated into a dosage form (step (d)). The formulations of the present invention may be prepared by well known technological processes, preferably the process involves a direct compression step, dry granulation and/or lyophilization. Preferably step (d) comprises direct compression. Direct compression, relative to other process technologies, has the advantage that it eliminates the need for water or alcohol, it optionally even avoids also other solvents or even any liquid substances, and therefore allows the formulation of solvent sensitive drugs. Furthermore, direct compression is the fastest and most cost effective way of tablet preparation. In order to carry out direct compression, a person skilled in the art can choose a suitable apparatus. With this respect it is known to a person skilled in the art that the force applied depends upon the size of the tablet. Suitable forces can for instance be in a range of from about 5 to about 30 kN, preferably of from about 10 to about 20 kN, and more preferably of from about 10 to about 15 kN. For example, in case the tablet exhibits a total mass of about 800 mg, and e.g. comprising about 10 mg ezetimibe and about 80 mg simvastatin, the optimal force is in a range from about 10 to about 15 kN, preferably the force is around 12 kN.

A dosage form according to the present invention is preferably in solid form, including tablets, capsules (soft or hard capsules), caplets, lozenges, and sachets. A dosage form according to the present invention is preferably in the form of a tablet. Furthermore, the dosage form can comprise a coating. Suitable coatings are known in the art, e.g. film coatings, which prevent environmental gases to ingress into the cores. Furthermore, the dosage form can be a multi-, bi- or mono-layered tablet.

Preferably the dosage form contains ezetimibe in doses of 1 mg, 2 mg, 5 mg, 7 mg, 10 mg, 12 mg, 15 mg or 20 mg, more preferably of 5 mg, 7 mg, 10 mg or 12 mg, even more preferably of 7 mg or 10 mg and most preferably of 10 mg.

If simvastatin is additionally used for preparing the dosage form according to the invention, preferably simvastatin is used in doses of 5 mg, 10 mg, 20 mg, 30 mg, 40 mg, 50 mg, 60 mg, 70 mg, 80 mg, 90 mg or 160 mg, and more preferably of 10 mg, 20 mg, 40 mg or 80 mg.

In one embodiment of the process according to the invention, optionally no water or alcohol, or optionally even no solvent or liquid substance at all is used. With respect to the present invention, the expression "solvent" as used herein refers to any liquid which is able to dissolve ezetimibe. For example, ezetimibe is soluble in organic solvents such as methanol, ethanol, or acetone, and poorly soluble in water.

The present invention further relates to a process for preparing a dosage form comprising ezetimibe, the process comprising the steps of:
a) providing a composition comprising ezetimibe, optionally blended with excipients, preferably with hydrophilic excipients,
b) sieving a composition comprising a composition provided by step (a),
c) direct compression of the composition after step (b).

With respect to this embodiment of the invention, the process steps of providing a composition, sieving a composition and direct compression of a composition can be carried out as described above. Additionally preferred, the shear mixing step as described above can be applied after the sieving step (b) and before direct compression step (c).

In this embodiment of the invention, preferably no water or alcohol, further preferred no solvent and even further preferred no liquid substance is used. Contrary thereto, known methods for preparing formulations containing ezetimibe mostly use wet granulation, which is the method of choice for the preparation of ezetimibe/simvastatin combinations in the known patent and scientific literature. The method is used to prepare granules, which were considered to be more suitable for compaction than powders and to provide uniform distribution of antioxidants used in the process. Although even if no antioxidants are used in the process, wet granulation had been contemplated as the method of choice. While wet granulation does provide granules which are more suitable for compaction than powders, the method requires several additional steps in the preparation of final dosage form. Firstly, the powder mass has to be wetted in order to prepare granulates, a step which exposes drug substances to water and/or organic solvents. Secondly, the prepared granulate has to be dried, which is a process which requires a sizable amount of time and is highly energy demanding. Both steps thus greatly decrease the economic efficacy of the process and pose additional problem in regard of stability (presence of water, increased temperature), safety (explosion risk when using organic solvents) and residual solvents (in the case of organic solvents).

The proposed solution offers a formulation which is prepared by time and cost effective direct compression and ensures suitable dissolution properties of final dosage form, which are otherwise not easily obtainable with direct compression.

Furthermore, the present invention relates to a dosage form, obtained according to the process of the invention as described above.

The dosage form according to the invention can be used in the prophylaxis or treatment of hypercholesterolemia.

Furthermore, the present invention refers to a composition comprising ezetimibe, obtained according to a process comprising the steps of:
a) sieving a composition comprising ezetimibe, optionally blended with hydrophilic excipients
b) shear mixing of the composition after step (a) to provide a fine particle distribution, preferably the shear mixing of the composition is carried out by high shear mixing. The process steps of sieving and shear mixing the composition can be carried out as described above. In one embodiment, the composition is obtained under dry conditions, preferably the process does not comprise the addition of water or alcohol, preferably no solvent is added, and optionally no liquid substance is added. Preferably the process comprises formulating dosage forms by direct compression.

The composition comprising ezetimibe according to the invention can be used in the prophylaxis or treatment of hypercholesterolemia.

The present invention further relates to a composition comprising ezetimibe and simvastatin, obtained according to a process comprising the steps of:

a) sieving a composition comprising ezetimibe, optionally blended with hydrophilic excipients b) mixing of the composition after step (a) to provide a fine particle distribution, preferably the mixing of the composition is carried out by shear mixing, wherein simvastatin can be added prior or after step a), preferably during step b). Again, the process steps of sieving and mixing the composition can be carried out as described above. With regard to the hydrophilic excipients that can optionally be used for blending, reference is made to the description above. In terms of beneficial coaction between ezetimibe and simvastatin, it is relevant that the ezetimibe exhibits a good dissolution profile, especially a fast dissolution rate. This can be provided by the combined composition according to the invention.

Further, in a preferred embodiment the composition containing ezetimibe and simvastatin is prepared according to a process, wherein the process does not comprise the addition of water or alcohol, preferably no solvent is added, even further preferred, no liquid substance is added. This is particularly advantageous, as simvastatin is known to be a water and solvent sensitive drug with reduced stability in case of water or solvents are used during the preparation process.

In a further preferred embodiment, the composition containing ezetimibe and simvastatin is formulated into a dosage form as described above, preferably after the mixing step has been carried out. Preferably, the formulation comprises direct compression, which is the fastest and most cost effective way of tablet preparation. In addition, by using direct compression, the use of water or solvent can be avoided, which leads to an improved stability of simvastatin compared to other formulation processes.

The following examples illustrate the process of the present invention and are not intended to limit the scope of the invention set forth in the claims appended hereto.

EXAMPLES

Comparison Between Blends Prepared According to the Invention and Prepared According to Known Methods A sample consisting of 80 g of ezetimibe and 320 g of spray dried lactose was blended in a conical blender for 5 minutes and the resulting blend (Blend 1) was analyzed in terms of the dissolution profile of ezetimibe.

The blend (Blend 1, comparative example) was further sieved through a sieve three times and the resulting blend (Blend 2, comparative example) was analyzed in terms of the dissolution profile of ezetimibe.

The remaining blend (Blend 2) was further mixed in a high shear mixer for 5 minutes and the resulting blend (Blend 3, according to the invention) was analyzed in terms of the dissolution profile of ezetimibe.

Figure 1:
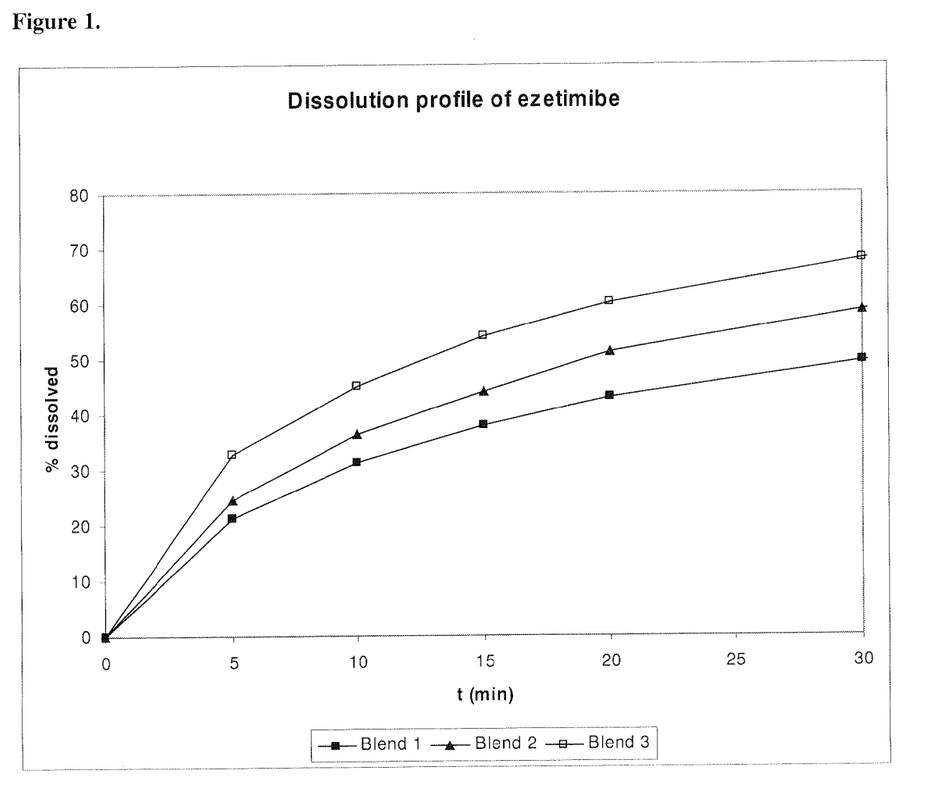
FIG. 1 shows the effect of different technological steps on the dissolution of ezetimibe.

All blend samples were analyzed on an USP Apparatus 2 (paddles) in 0.01 M HCl and 0.25% sodium lauryl sulfate and are shown of FIG. 1.

Particle size of ezetimibe was determined by Malvern Mastersizer and are given in Table 1. The lactose in the blend was dissolved and therefore did not interfere with the size measurements.

After mixing of blend 2 in a high shear mixer, a good particle distribution could be reached. The size of the ezetimibe particles was not essentially changed.

TABLE 1

Particle size of ezetimibe during different technological steps.

| Sample | Particle size d(0.9) | Particle size d(0.5) | Particle size d(0.1) |
|---|---|---|---|
| Starting ezetimibe | 16.87 μm | 7.54 μm | 0.43 μm |
| Blend 2 | 21.33 μm | 10.86 μm | 0.49 μm |
| Blend 3 | 22.28 μm | 10.01 μm | 0.41 μm |

Comparison of Tablets Prepared According to the Invention and According to Known Methods The composition of the tablets is given in table 2 below.

TABLE 2

| Substance | Amount per tablet (mg) |
|---|---|
| Ezetimibe | 10.00 |
| Simvastatin | 80.00 |
| Microcrystalline cellulose | 160.00 |
| Spry dried lactose | 504.00 |
| Croscarmellose sodium | 16.00 |
| Hydroxypropyl cellulose | 16.00 |
| Colloidal silica | 6.00 |
| Magnesium stearat | 8.00 |
| Total mass of the tablet (mg) | 800.00 |

Manufacturing Procedure 1

Comparative Example

Ezetimibe was blended with spray dried lactose and mixed in a high shear mixer. Simvastatin, microcrystalline cellulose, croscarmellose sodium, hydroxypropyl cellulose and colloidal silica were added in the high shear mixer and the mixture was mixed again. The resulting mixture was sieved through a sieve, blended with magnesium stearate and compressed into tablets (tablets 1).

Manufacturing Procedure 2

Example According to the Invention

Ezetimibe was blended with spray dried lactose and sieved through a sieve. Sieved mixture was mixed in a high shear mixer. Simvastatin, microcrystalline cellulose, croscarmellose sodium, hydroxypropyl cellulose and colloidal silica were added in the high shear mixer and the mixture was mixed again. The resulting mixture was sieved through a sieve, blended with magnesium stearate and compressed into tablets (tablets 2).

Figure 2:
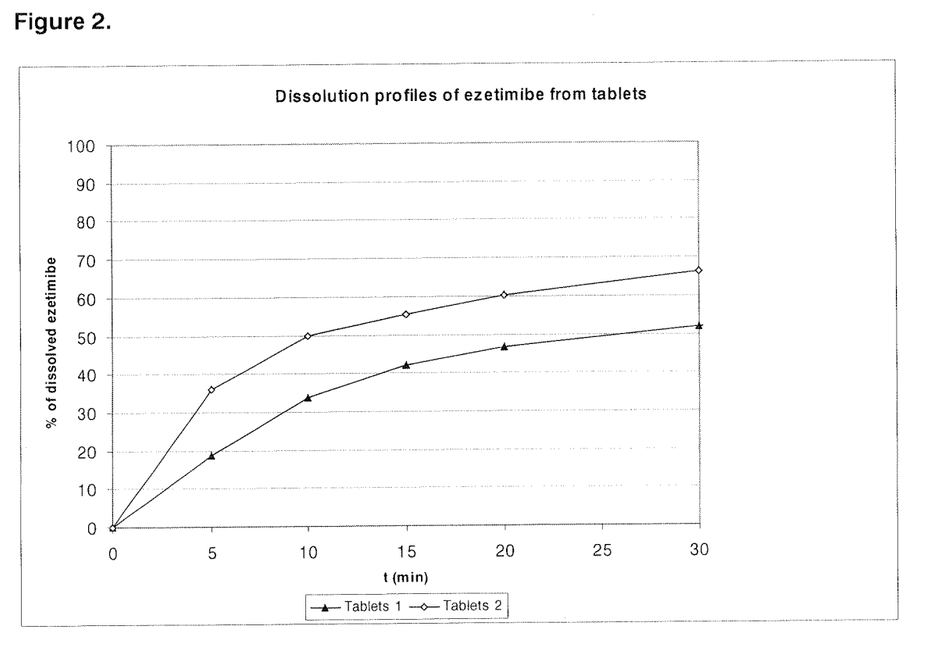
FIG. 2 shows the effect of sieving on the dissolution of ezetimibe.

All tablet samples were analyzed on an USP Apparatus 2 (paddles) in 0.01 M HCl and 0.25% sodium lauryl sulfate and are shown in FIG. 2. FIG. 2 shows the improved dissolution properties of the tablets prepared according to the invention.

The invention claimed is:

1. A process for preparing a dosage form, the process consisting essentially of the steps:
 (a) providing a starting composition of particulates of ezetimibe and a hydrophilic excipient,
 (b) sieving a composition provided by step (a),
 (c) high shear mixing of the composition after step (b), and
 (d) formulation into a dosage form by direct compression, wherein said high shear mixing is carried out at a paddle speed of at least 100 RPM; wherein step (b) occurs before step (c); wherein the size of the particles d (0.9) of ezetimibe in the starting composition is between 8 and 25 μm and is essentially unchanged during the process; wherein the process is conducted under dry conditions without a solvent; wherein after (c) no further ingredients are added and no further mixing or sieving is performed; and wherein, when the produced dosage form is analyzed in a USP Apparatus 2 (paddles) in 0.01 M HCl and 0.25% sodium lauryl sulfate, more than 50% dissolves within 15 minutes.

2. The process according to claim 1 wherein the ezetimibe:hydrophilic excipient weight ratio is in a range of from about 1:1 to about 1:100.

3. The process according to claim 1 wherein the hydrophilic excipient is selected from the group consisting of polyethylene glycols, poloxamers, polysaccharides, saccharides and mixtures thereof.

4. A process for preparing a dosage form, the process consisting essentially of the steps:
 (a) providing a starting composition of particulates of ezetimibe and a hydrophilic excipient,
 (b) sieving a composition provided by step (a),
 (c) high shear mixing of the composition after step (b) wherein simvastatin and optionally at least one further excipient is added to the composition during the high shear mixing, and
 (d) formulation into a dosage form by direct compression, wherein said high shear mixing is carried out at a paddle speed of at least 100 RPM; wherein step (b) occurs before step (c); wherein the size of the particles d (0.9) of ezetimibe in the starting composition is between 8 and 25 μm and is essentially unchanged during the process; wherein the process is conducted under dry conditions without a solvent; wherein after (c) no further ingredients are added and no further mixing or sieving is performed; and wherein, when the produced dosage form is analyzed in a USP Apparatus 2 (paddles) in 0.01 M HCl and 0.25% sodium lauryl sulfate, more than 50% dissolves within 15 minutes.

5. A process for preparing a dosage form, the process consisting essentially of the steps:
 (a) providing a starting composition of particulates of ezetimibe and a hydrophilic excipient,
 (b) sieving a composition comprising a composition provided by step (a),
 (c) high shear mixing of the composition after step (b) wherein at least one further excipient is added to the composition during the high shear mixing, and
 (d) formulation into a dosage form by direct compression, wherein said high shear mixing is carried out at a paddle speed of at least 100 RPM; wherein step (b) occurs before step (c); wherein the size of the particles d (0.9) of ezetimibe in the starting composition is between 8 and 25 μm and is essentially unchanged during the process; wherein the process is conducted under dry conditions without a solvent; wherein after (c) no further ingredients are added and no further mixing or sieving is performed; and wherein, when the produced dosage form is analyzed in a USP Apparatus 2 (paddles) in 0.01 M HCl and 0.25% sodium lauryl sulfate, more than 50% dissolves within 15 minutes.

6. The process according to claim 1 wherein the size of the sieve is between 125 mesh and 4 mesh.

7. A composition comprising only ezetimibe as the active ingredient, wherein the ezetimibe has not been milled and wherein when the composition is analyzed in a USP Apparatus 2 (paddles) in 0.01 M HCl and 0.25% sodium lauryl sulfate, more than 50% dissolves within 15 minutes; wherein the composition is made by the process according to claim 1.

8. A method of treating hypercholesterolemia comprising administering to a patient in need thereof an effective amount of a composition according to claim 7.

9. A composition consisting essentially of ezetimibe and simvastatin, wherein the ezetimibe has not been milled and wherein when the composition is analyzed in a USP Apparatus 2 (paddles) in 0.01 M HCl and 0.25% sodium lauryl sulfate, more than 50% dissolves within 15 minutes; wherein the composition is made by the process according to claim 4.

* * * * *